US012630885B2

(12) United States Patent
Wickenberg et al.

(10) Patent No.: US 12,630,885 B2
(45) Date of Patent: May 19, 2026

(54) VIABILITY DETECTION AND QUANTIFICATION ASSAY OF WATERBORNE PATHOGENS BY ENRICHMENT

(71) Applicants: Leah Wickenberg, Reno, NV (US); Katherine Fisher, Reno, NV (US); William F. McCoy, Reno, NV (US)

(72) Inventors: Leah Wickenberg, Reno, NV (US); Katherine Fisher, Reno, NV (US); William F. McCoy, Reno, NV (US)

(73) Assignee: Phigenics, LLC

( * ) Notice: Subject to any disclaimer, the term of this patent is extended or adjusted under 35 U.S.C. 154(b) by 143 days.

(21) Appl. No.: 16/729,422

(22) Filed: Dec. 29, 2019

(65) Prior Publication Data

US 2020/0208200 A1 Jul. 2, 2020

Related U.S. Application Data

(60) Provisional application No. 62/786,965, filed on Dec. 31, 2018.

(51) Int. Cl.
| | |
|---|---|
| *C12Q 1/68* | (2018.01) |
| *B01D 69/02* | (2006.01) |
| *B01D 71/50* | (2006.01) |
| *C12Q 1/6806* | (2018.01) |
| *C12Q 1/686* | (2018.01) |
| *C12Q 1/689* | (2018.01) |

(52) U.S. Cl.
CPC ............ *C12Q 1/689* (2013.01); *B01D 69/02* (2013.01); *B01D 71/50* (2013.01); *C12Q*

*1/6806* (2013.01); *C12Q 1/686* (2013.01); *B01D 2325/02834* (2022.08); *C12Q 2561/113* (2013.01)

(58) Field of Classification Search
None
See application file for complete search history.

(56) References Cited

U.S. PATENT DOCUMENTS 9,518,994 B2 * 12/2016 Gozes ................ G01N 33/6896
2007/0218522 A1 * 9/2007 McCoy .................... C12Q 1/04
435/34

(Continued)

OTHER PUBLICATIONS

Toplitsch et al. (2018). Legionella detection in environmental samples for successful implementation of qPCR. Water, vol. 10:1012, p. 1-11.*

(Continued)

*Primary Examiner* — Stephanie K Mummert
(74) *Attorney, Agent, or Firm* — Ian Burns; Darren Gardner; American Law, Ltd.

(57) ABSTRACT

A process for detecting viable waterborne pathogens in a water sample, includes enriching a concentrate of bacteria from the sample and taking a first DNA extract at time $T_0$ and a second DNA extract at time $T_2$ after an incubation period. Real-time polymerase chain reaction performed on the DNA extracts yields respective cycle threshold values Ct. The change in Ct provides an indication of the targeted pathogen in the sample. An order of magnitude quantification of the sample can also be performed using a serial dilution technique on the $T_0$ DNA extract. The process has particular application for detecting *Legionella*, including viable but not culturable cells.

25 Claims, 8 Drawing Sheets

(56)        References Cited

U.S. PATENT DOCUMENTS

| 2009/0239256 | A1* | 9/2009 | Giglio | B01J 39/04 |
| | | | | 435/34 |
| 2019/0262469 | A1* | 8/2019 | Brinker | A61K 47/6923 |
| 2019/0290800 | A1* | 9/2019 | Pesce | D05C 17/00 |

OTHER PUBLICATIONS

Yang et al. (FEMS Immunology and Medical Microbiology, 2003, vol. 38, 265-271) (Year: 2003).*
Pitkanen et al. (Can J Microbiol, 2009, 55:849-858) (Year: 2009).*
Antonov et al. (Laboratory Investigation, 2005, 85:1040-1050) (Year: 2005).*
Robinson et al. (Veterinary Immunology and Immunopathology, 2007, 115:160-165) (Year: 2007).*
Kim et al. (Ann Lab Med, 2014, 34:203-209) (Year: 2014).*
Nocker et al. (J of Microbiol Methods, 2007, 70:252-260) (Year: 2007).*

* cited by examiner

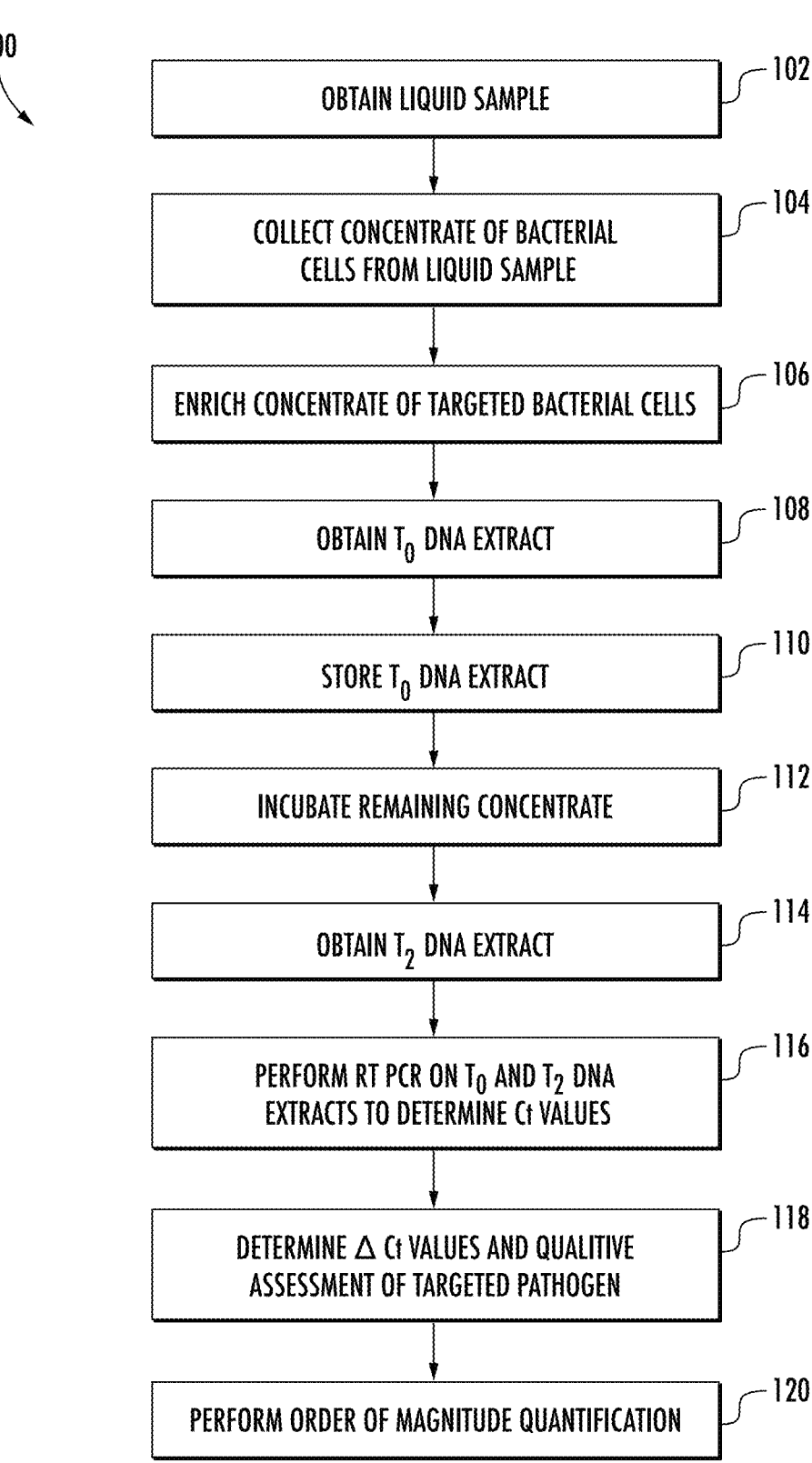

100

OBTAIN LIQUID SAMPLE — 102

COLLECT CONCENTRATE OF BACTERIAL CELLS FROM LIQUID SAMPLE — 104

ENRICH CONCENTRATE OF TARGETED BACTERIAL CELLS — 106

OBTAIN $T_0$ DNA EXTRACT — 108

STORE $T_0$ DNA EXTRACT — 110

INCUBATE REMAINING CONCENTRATE — 112

OBTAIN $T_2$ DNA EXTRACT — 114

PERFORM RT PCR ON $T_0$ AND $T_2$ DNA EXTRACTS TO DETERMINE Ct VALUES — 116

DETERMINE $\Delta$ Ct VALUES AND QUALITIVE ASSESSMENT OF TARGETED PATHOGEN — 118

PERFORM ORDER OF MAGNITUDE QUANTIFICATION — 120

302 — DILUTE $T_0$ DNA EXTRACT

304 — PERFORM RT-PCR ON DILUTION

306 — DILUTION SHOWS PCR AMPLIFICATION ?

YES

NO

308 — QUANTIFY TARGETED PATHOGEN FROM HIGHEST DILUTION THAT SHOWED PCR AMPLIFICATION

VIABILITY DETECTION AND QUANTIFICATION ASSAY OF WATERBORNE PATHOGENS BY ENRICHMENT

CROSS REFERENCE TO RELATED APPLICATIONS

This application claims priority to U.S. provisional patent application Ser. No. 62/786,965 filed 31 Dec. 2019, the contents of which are herein incorporated by reference

FIELD OF THE INVENTION

The present invention relates to methods and compositions for performing biological assays. Specifically, the invention relates to the detection of waterborne pathogens, for example *Legionella*. This technology may be used for a variety of biological applications, including nucleic acid amplification, as well as other biological assays and reactions.

BACKGROUND OF THE INVENTION

Finding a laboratory bacterial growth media for environmental samples that will decrease and/or eliminate the growth of competing microbiota and yet augment the growth of the target organism is the constant compromise that is made in microbiology laboratories (Deadre et al., 1998). In contrast; there are molecular detection methods, namely real-time Polymerase Chain Reaction (PCR), that can deliver results pertaining to the presence or absence of bacterial DNA in hours. Deoxyribonucleic acid (DNA) is the hereditary material in humans and most all other organisms. The cell nucleus contains most of the DNA (nuclear DNA), however a small amount of DNA can also be found in the mitochondria (mitochondrial DNA or mtDNA) (U.S. Department of Health & Human Services, *What is DNA?* (2018)). Bacterial cells do not contain a nucleus, therefore, the DNA is contained in the cytoplasm (cytoplasmic DNA). When using real-time PCR, a positive result is produced when the fluorescent signal crosses the calculated threshold value. The more DNA present in the sample at the start of the reaction, the fewer cycles it takes to cross the threshold. However; these molecular detection methods cannot differentiate between viable, non-viable, and/or viable but not culturable (VBNC) cells without additional sample preparation steps and/or assays.

Many bacterial genera and species have been found to exist in a viable but non-culturable (VBNC) state. The term "culturable" refers to the capacity of bacterial cells to replicate on agar-based solid growth media to such an extent so that colonies of bacterial cells can be then observed, counted, isolated and further analyzed. Since this discovery in 1982, cells that are viable but non-culturable (VBNC) are characterized by a loss of culturability on routine solid growth media. This loss of culturability on routine solid growth media results in an impairment of accurate identification by conventional plate count techniques, which leads to an underestimation of total viable cells in environmental or clinical samples, and thus poses a risk to public health. It has been found that the induction of the VBNC state in bacteria may be a result of exposure to various stresses. It should also be noted that VBNC cells may be resuscitated back to culturable cells under suitable stimuli (U.S. National Library of Medicine National Institutes of Health, the Importance of the viable but non-culturable state in human bacterial pathogens (2014)). These limitations are what have led researchers to embark on a journey for a more suitable definition of the word "viable" and faster ways to measure it.

Currently, there are four main approaches to measure viability of cells beyond traditional microbiological methods. These include assays to: 1.) determine the level of membrane integrity, 2.) measure the concentration of Adenosine Triphosphate (ATP), 3.) measure the membrane potential of the cell, and 4.) measure of enzymatic activity (Grossi, Dey, & Ashbolt, 2018). Research has reported poor correlation between these assays and the traditional microbiological methods. This poor correlation is mainly attributed to the presence of cells in the viable but not culturable state (Ducret, Chabalier, & Dukan, 2014; Keserue, Baumgartner, Felleisen, & Egli, (2012)).

Some researchers have also proposed the use of mRNA targets for PCR. These molecules have a very short half-life in the cell when compared to DNA and can therefore indicate viability more accurately (Bej, Mahbubani, & Atlas, (1991)).

One of the most common assays available is the use of membrane impermeable dyes paired with real-time PCR detection to differentiate viable from non-viable cells. These assays rely on the principle that non-viable cells will not have intact membranes. The dye can then intercalate into the DNA of that cell and, upon photoactivation, will render that DNA unusable for the PCR reaction (Cangelosi & Meschke, (2014)). Studies have shown that Gram negative bacteria collected from systems disinfected with chlorine compounds do not exhibit significant alterations in membrane permeability when exposed to typical use dilutions (0.5-2 ppm) of chlorine. The concentration of chlorine compounds needed to be much higher (up to 50 ppm) before membrane destabilization was noted. This study also shows that water systems with high organic matter content give a certain amount of protection to the cell membrane, inhibiting the disinfection action of the chlorine compounds (Virto, Mafias, Lvarez, Condon, & Raso, (2005)). These studies indicate that relying solely on membrane permeability to distinguish between viable and non-viable cells is not adequate.

The present invention aims to resolve the need for a faster, more accurate test to determine the presence or absence of viable *Legionella* bacteria in a water system. Traditional methods via microbiological culture on laboratory solid growth media typically take 10-14 days for results (Centers for Disease Control and Prevention (CDC), 2005; "ISO 11731:2017," (2017)). These traditional methods rely on the conventional definition of "viable" as being the ability to produce colonies of bacteria on the surface of solid growth media such as is described in ISO 11731:2017). The present invention introduces an alternative culture-based method that correlate well with the traditional ISO 11731 method while also remarkably eliminating the issues of VBNC cells.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to qualify the presence of targeted pathogens in a water sample;

determine the presence of viable but not culturable (VBNC) bacterial cells in a water sample;

provide a quantification of targeted pathogens in a water sample, including viable but not culturable bacterial cells;

detect targeted pathogens in water sample with high sensitivity and accuracy;

provide a method for analyzing a water sample for targeted pathogens that is faster than prior art techniques;

provide a fast method for determining the presence of viable *Legionella* within a water sample.

These and other advantages may be realized by reference to the remaining portions of the specification, claims, and abstract.

BRIEF DESCRIPTION OF ONE EMBODIMENT OF THE PRESENT INVENTION

In one aspect of the present invention, there is a provided a process for detecting presence of viable targeted waterborne pathogens. The method may comprise obtaining a liquid sample, collecting a concentrate of bacterial cells from the liquid sample. The concentrate may be enriched to produce an enriched concentrate of bacterial cells. A $T_0$ DNA extract may be extracted from the enriched concentrate of bacterial cells at time $T_0$ and stored. The remaining enriched concentrate may be incubated in liquid growth media and then at time $T_2$, a $T_2$ DNA extract may be extracted from the enriched concentrate. The method may comprise analyzing the $T_0$ DNA extract with real-time Polymerase Chain Reaction (PCR) to determine a cycle threshold (Ct) value for the $T_0$ DNA extract and analyzing the $T_2$ DNA extract with real-time Polymerase Chain Reaction (PCR) to determine a Ct value for the $T_2$ DNA extract. A difference in the Ct value between the $T_0$ DNA extract and the $T_2$ DNA extract may be analyzed to determine a qualitative assessment of the presence of viable waterborne pathogens in the liquid sample.

In one aspect of the present invention, there is a provided a process for detecting presence of viable targeted waterborne pathogens. The process may comprise step for obtaining a liquid sample, step for collecting a concentrate of bacterial cells from the liquid sample, step for enriching the concentrate of bacterial cells to produce an enriched concentrate of bacterial cells, step for extracting a $T_0$ DNA extract from the enriched concentrate of bacterial cells at time $T_0$, step for storing the $T_0$ DNA extract, step for incubating the enriched concentrate of bacterial cells, step for extracting a $T_2$ DNA extract from the incubated enriched concentrate of bacterial cells at time $T_2$, step for analyzing the $T_0$ DNA extract with real-time Polymerase Chain Reaction (PCR) to determine a Ct value for the $T_0$ DNA extract, step for analyzing the $T_2$ DNA extract with real-time Polymerase Chain Reaction (PCR) to determine a Ct value for the $T_2$ DNA extract, and step for analyzing a difference in Ct value ($\Delta$Ct) between the $T_0$ DNA extract and the $T_2$ DNA extract to determine a qualitative assessment of the presence of viable waterborne pathogens in the liquid sample.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 1 illustrates flowchart of a process for determining a presence of target pathogens in a liquid sample;

DESCRIPTION OF CERTAIN EMBODIMENTS OF THE PRESENT INVENTION

Figure 2:
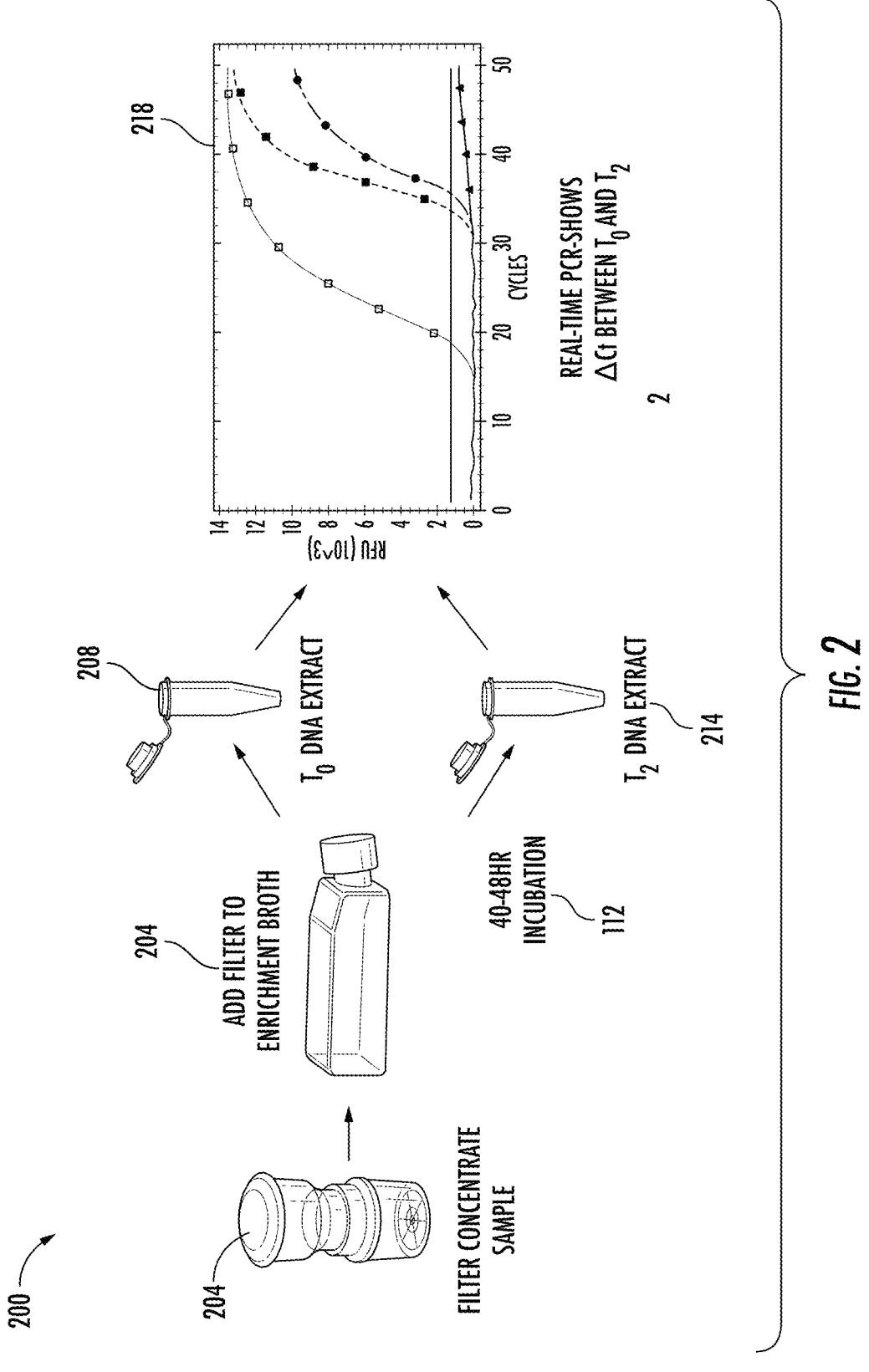
FIG. 2 is substantially a schematic process of the flowchart of FIG. 1.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

PVT-VIABLE means Phigenics Validation Test-Viability Identification Assay by *Legionella* Enrichment.

(LOD) means Limit of Detection.

(VBNC) means Viable But Not Culturable.

(CFU) means Colony-Forming Unit.

(Ct) means the Cycle Threshold values. Cq may be used interchangeably with Ct to also refer to the Cycle Threshold value.

(PCR) means Polymerase Chain Reaction.

$T_0$ DNA extract means a neat DNA extraction that occurs before the time of incubation.

(PBS) means Phosphate Buffered Saline.

$T_2$ DNA extract means DNA extractions after a period of incubation.

$T_0/T_2$ represents a period of incubation between the $T_0$ DNA extract and the $T_2$ DNA extract, commonly, though not exclusively, a 40 h-48 h time gap.

EB7 means a modified Buffered Yeast Extract (BYE) media. The EB7 constitutes the following, Vancomycin, Polymyxin B, Cycloheximide, Glycine, Iron pyrophosphate, L-cysteine hydrochloride, and bovine serum albumin.

Deoxyribonucleic acid (DNA) synthesis is a cellular function common to all living organisms during cell division. With every cell division the amount of DNA doubles and this process only occurs when cells divide (Huisman & D'Ari, (1981)). DNA can be detected via polymerase chain reaction (PCR), a technique that amplifies a segment of DNA to reach detectable limits. This reaction uses a polymerase to add nucleotides to the strand starting at a specific primer sequence (Saiki et al., (1988)).

Traditional PCR requires post reaction analysis to determine a positive or negative reaction. In contrast, real-time PCR (RT-PCR) monitors the reaction as it progresses using fluorescent probes.

Clinical microbiology laboratories have been revolutionized by real-time PCR technology enabling human microbial infection diagnostic capabilities. The real-time PCR testing method utilizes a combination of PCR chemistry with fluorescent probe detection of amplified product in the same reaction vessel (U.S. National Library of Medicine National Institutes of Health, Real-Time PCR in Clinical Microbiology: Applications for Routine Laboratory Testing (2006)).

When using real-time PCR, a positive signal is produced when the fluorescent signal crosses the calculated threshold value. The more DNA present in the sample at the start of the reaction, the fewer cycles it takes to cross the threshold. Thus, a lower Cycle threshold Ct value depicts a higher starting concentration of DNA. A higher starting concentration of DNA is indicative of a higher starting concentration of cells. Equipment for real-time PCR procedures is known in the art. In one particular embodiment, the PCR equipment may include the Bio-Rad CFX 96 Deep Well Touch.

Legionella

A gram-negative Bacillus was isolated from infected patients of the 1976 American Legion convention in Philadelphia, PA. This Bacillus would later be identified as Legionella, which is also characterized as non-acid fast, heterotrophic, aerobic and catalase positive (McCoy, (2005)). Legionella is a very common waterborne pathogenic bacterium, for example, a study done in Ontario, Canada showed that 55% of building water tested positive for Legionella pneumophila (Dutka & Walsh, (1984)). These bacteria proliferate in host cells like Acanthamoeba and human alveolar macrophages during infection (Percival & Williams, (2014)). There are over 60 species within the genus Legionella and 70 serogroups (Cunha, 2010a; Morita et al., (2017)). Legionella bacteria are the cause of legionellosis, an atypical form of pneumonia caused aspiration of contaminated water by susceptible populations. Pontiac Fever, also caused by Legionella, is a mild, flu-like form of legionellosis that can occur in healthy populations (Cunha, 2010b).

Enrichment of Target Organisms

Most standard detection methods for foodborne pathogens (Bacteriological Analytical Methods, BAM) require a pre-enrichment step with non-selective or selective growth media. This is true for Shiga toxin producing E. coli, Listeria monocytogenes, Salmonella spp., and others; Myint, Johnson, Tablante, & Heckert, (2006)). These enrichment procedures are used to increase the bacterial load in a sample to a detectable level for further analysis. The analysis steps are usually composed of a mixture of traditional culture assays, biochemical assays, and molecular assays that are specific to the target organism, but they all have one factor in common, the analysis of the sample takes place after the enrichment period.

For the present invention the test hypothesis was whether two technologies could be combined to analyze building water samples for viable Legionella. The two technologies in question were the theory of enrichment of a sample and the analysis of the concentration of DNA, via RT-PCR, at two timepoints during the enrichment period in liquid media.

The above described strategy presented multiple complications, the first being the selective enrichment of Legionella from water that was possibly contaminated with highly competitive background microbiota. This was accomplished by titrating the typical antibiotics used for Legionella culture on solid media, glycine, vancomycin, polymyxin B, and cycloheximide.

Surprisingly, the titration of these selective agents allowed for the selective enrichment and targeting of Legionella while decreasing the growth of the background microbiota. For highly contaminated samples the background microbiota was not eliminated. Additional steps are needed to address water samples with a high bacterial load. The second issue that needed to be resolved was to determine the positive predictive value of this assay when compared to the traditional culture methods. Curiously, the data show that the PPV of PVT-VIABLE when compared to the traditional ISO 11731 method is low. Many more positive samples were observed using the PVT-VIABLE assay. This is attributed to the unanticipated ability of PVT-VIABLE to resuscitate VBNC cells.

A flowchart 100 of a PVT-VIABLE process in accordance with an embodiment of the present application is depicted in FIG. 1. The process 100 is depicted schematically at 200 in FIG. 2. The process 100 includes obtaining a liquid sample (step 102). In a practical real-world analysis, obtaining the sample may include sampling a water source and shipping the sample to a laboratory or test site where the analysis is to be conducted. To simulate the water sampling process within the laboratory, e.g. for generating calibration and comparative data, a water sample obtained within the laboratory may be allowed to stand at room temperature for a period of time, e.g. 24 hours, to simulate shipping.

At the laboratory or testing site, the process 100 includes collecting a concentrate of bacterial cells from the liquid sample (step 104) and enriching the concentrate of bacterial cells to produce an enriched concentration of the targeted bacterial cells (step 106). As shown in FIG. 2, the concentrate may be obtained by filter concentration of the sample 204 followed by inoculation of the sample concentrate into a nutrient rich growth environment 206 to produce the enriched concentrate of the bacterial cells. In alternative embodiments, collection of the bacterial concentrate may be completed by centrifugation, or any other method known in the art provided that cell damage is limited through the collection process.

A $T_0$ DNA extract 208 is extracted (step 108) from the enriched concentrate of bacterial cells at time $T_0$ and stored 110. The remaining enriched concentrate is then incubated 112 for an incubation period. At time $T_2$ after the incubation period, a $T_2$ DNA extract 214 is extracted from the enriched concentrate (step 114). Real-time PCR is then performed on the $T_0$ DNA extract and $T_2$ DNA extract to determine a cycle threshold Ct for each of the DNA extracts (step 116).

After completion of the RT-PCR process the data from the report is analyzed. The Ct values of each timepoint for each sample are assessed and compared. A decrease in Ct value from $T_0$ to $T_2$ corresponds to an increase in nucleic acid concentration. An increase in Ct value indicates a decrease in nucleic acid concentration. Therefore, any significant decrease in Ct value indicates growth of the cell population that was inoculated into the broth. The indication of cell growth may be an indicator of the presence of viable *Legionella* or other targeted pathogen.

At step 118, the difference in the Ct value ($\Delta$Ct) between the $T_0$ DNA extract and $T_2$ DNA extract is analyzed to provide a qualitative assessment 218 of the presence of the targeted waterborne pathogens for the sample, such as viable *Legionella*.

An order of magnitude quantification of the targeted pathogens (step 120) can optionally be performed using a serial dilution technique described in more detail below.

Samples of both potable and non-potable water can be analyzed for *Legionella* and other waterborne pathogens using this method. In one embodiment, sample size is between 100-1000 ml in volume and collected in sterile containers containing sodium thiosulfate to neutralize any residual disinfectant in the sample. Prior to shipping, the sample may be treated to neutralize residual oxidants and antimicrobials to provide a substantially oxidant-free sample. It should be noted that all collection containers should be sterilized in a manner that is consistent with degradation of any DNA. Simple sterilization to prohibit the growth of living organisms may be insufficient. Prompt delivery of the samples to the laboratory or testing site is beneficial to ensure consistency and accuracy of results.

In one embodiment, the filter concentration process may include filtering a one hundred milliliter sample using a filtration unit having a 47 mm diameter track etched polycarbonate membrane, with a porosity of less than 0.4 m and preferably around 0.2 m. After the entire 100 ml has been filtered, the sample membrane is aseptically removed from the filter apparatus using sterile forceps. The membrane is placed into a cell culture flask containing 10 ml of an enrichment broth and is shaken by hand for 30 seconds to transfer the bacteria from the membrane into the enrichment broth.

The enrichment broth may be EB7 as defined above. In one embodiment, the EB7 is a modified BYE media comprising Vancomycin 0.25-0.4 g, Polymyxin 15,000-40,000 IU, Cycloheximide 15-40 mg, glycine 2-4 g as well as Iron pyrophosphate, L-cysteine hydrochloride, and bovine serum albumin. In one specific embodiment, the EB7 media includes Vancomycin (0.3375 mg), Polymyxin B (27,000 IU), Cycloheximide (27 mg), Glycine (3.0125 g), Iron pyrophosphate (0.25 g), L-cysteine hydrochloride (0.4 g), and bovine serum albumin (10 g). Alternative enrichment media may include R2A or 1395 broth, both of which are known in the art.

In one embodiment, the incubation period may be 40-48 hours. Greater or lesser periods may be used depending on various factors including type of pathogen under analysis, accuracy of results required, etc. During the incubation period, the cell culture flasks may be kept at a temperature from about 30° C. to about 37° C., preferably about 35° C. with shaking at 50 rpm.

In one embodiment, the $T_0$ and $T_2$ DNA extraction comprise taking a 2.0 ml aliquot of the broth and processing the aliquot via any appropriate DNA extraction method that gives PCR quality DNA. For example, the DNA extraction should yield acceptable 260/280 and 260/230 ratios and have an acceptable DNA concentration for PCR. In a particular embodiment, a proprietary DNA extraction method referred to as the Phigenics Ultra-Rapid DNA Extraction (P.U.R.E.™) may be used.

Figure 3:
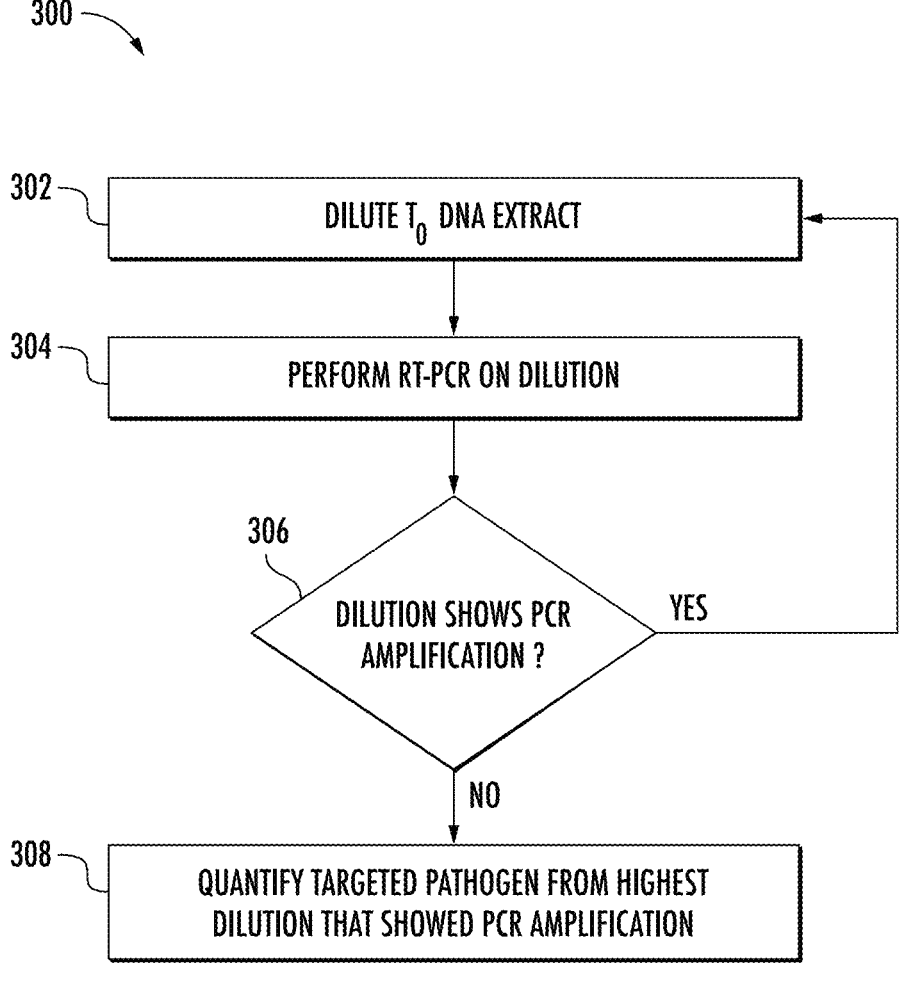
FIG. 3 is substantially a flowchart of an order of magnitude quantification method based on serial dilution.

FIG. 3 shows a flowchart 300 of a method for order of magnitude quantification of the targeted pathogen using a serial dilution technique. At step 302, the $T_0$ DNA extract is diluted and then a real-time PCR is performed on the dilution 304. If the dilution shows PCR amplification (decision 306), then the process returns to step 302 where further dilution occurs. Once the dilution ceases to show PCR amplification, the level of pathogen may be quantified 308 by analyzing the highest dilution that showed PCR amplification. That is, the highest dilution of the $T_0$ DNA extract at which PCR amplification is detected provides an order of magnitude quantification of the viable targeted waterborne pathogen in the liquid sample.

In one embodiment, the first dilution may be 10-fold to yield a 1:10 dilution. The second dilution may be a further 10-fold to yield a 1:100 dilution.

If only the original $T_0$ DNA extract shows PCR amplification, then the concentration X of targeted pathogen in the sample may be considered to be $\leq 1$ CFU/ml. If the 1:10 dilution is the highest dilution that shows PCR amplification, then the X may be considered to be within the range $1 < X \leq 10$ CFU/ml. If the 1:100 dilution is the highest dilution that shows PCR amplification, then the X may be considered to be within the range $10 < X \leq 100$ CFU/ml.

Greater resolution may be produced in the quantification if required by smaller serial dilutions.

Example 1—Pure Culture Tests

The PVT-VIABLE protocol was tested on four species of pure culture *Legionella* including lab strains *L. pneumophila* (ATCC 33823) and *L. longbeachae* (ATCC 33462), and environmentally isolated *L. micdadei* and *L. anisa*. Cell suspensions of each organism were prepared in sterile phosphate buffered saline (PBS) to an $OD_{600}$ of 0.05. Then each suspension was serially diluted to $10_{-3}$. Next, 10 µl of each dilution was added to 100 ml of PBS to simulate a water sample. Each 100 ml sample was analyzed by the PVT-VIABLE protocol.

Figure 4:
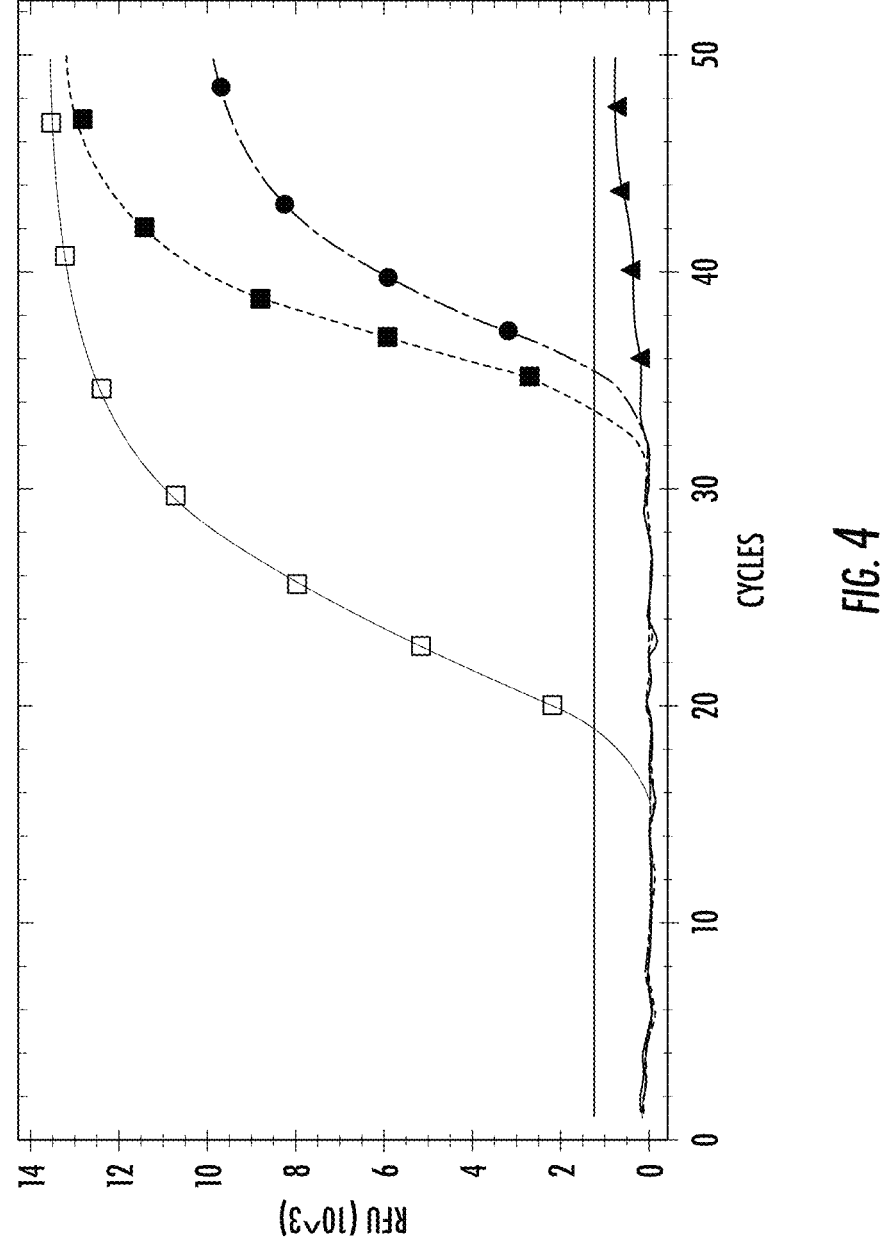
FIG. 4 substantially shows real-time PCR amplification curves for *Legionella pneumophila* (ATCC 33823) analyzed with PVT-VIABLE.

FIG. 4 shows the real-time PCR amplification curves for the $10_{-2}$ dilution of *L. pneumophila* analyzed by the PVT-VIABLE process. A dilute cell suspension of *Legionella pneumophila* was made in sterile PBS and analyzed with the PVT-VIABLE protocol. DNA was extracted at $T_0$ and $T_2$. The $T_0$ DNA extract was stored at $-20°$ C. to preserve the state of the DNA in the $T_0$ DNA extract until $T_2$ when the extracts were analyzed by real-time PCR. The difference ($\Delta$Ct) between the $T_0$ Ct (filled squares) and the $T_2$ Ct (open squares) was 14.62. In FIG. 4, a positive control is indicated by the filled circles and a negative control is indicated by the filled triangles.

Figure 5:
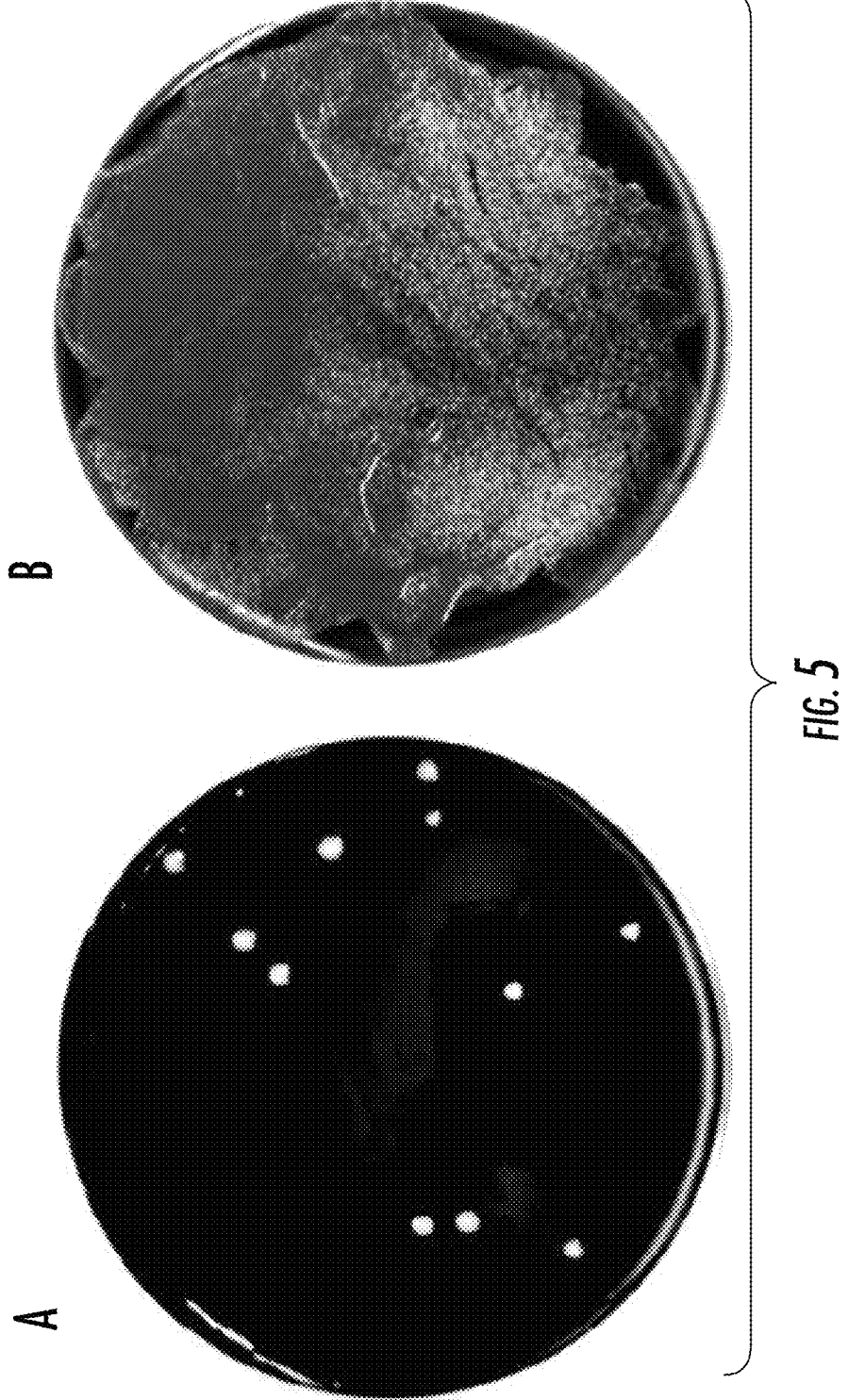
FIG. 5 substantially shows spread plates for *Legionella pneumophila* (ATCC 33823) analyzed with PVT-VIABLE.

For comparative analysis and to prove the feasibility of the PVT-VIABLE process, traditional plating of the sample may also be conducted. FIG. 5 shows the corresponding spread plates for *Legionella pneumophila* (ATCC 33823) for the sample analysis using the PVT-VIABLE process illustrated in FIG. 4. Spread plates were prepared for the $T_0$ extract (A. in FIG. 5) and for the $T_2$ extract (B. in FIG. 5).

As stated, the $\Delta$Ct was 14.62 which was very high, but normal for a lab strain sample that did not have any competing microorganisms. Similarly, the spread plates for this sample (FIG. 5) show a great deal of growth in the broth culture. All species tested grew well in EB7 and had $\Delta$Ct greater than 1.5.

Example 2—Environmental Sample Tests

PVT-VIABLE was tested on 301 environmental water samples. Water samples were collected from multiple building water systems and analyzed with the PVT-VIABLE protocol. DNA was extracted at $T_0$ and $T_2$. The $T_0$ DNA extract was kept at $-20°$ C. until $T_2$ when the extracts were analyzed by real-time PCR.

Figure 6:
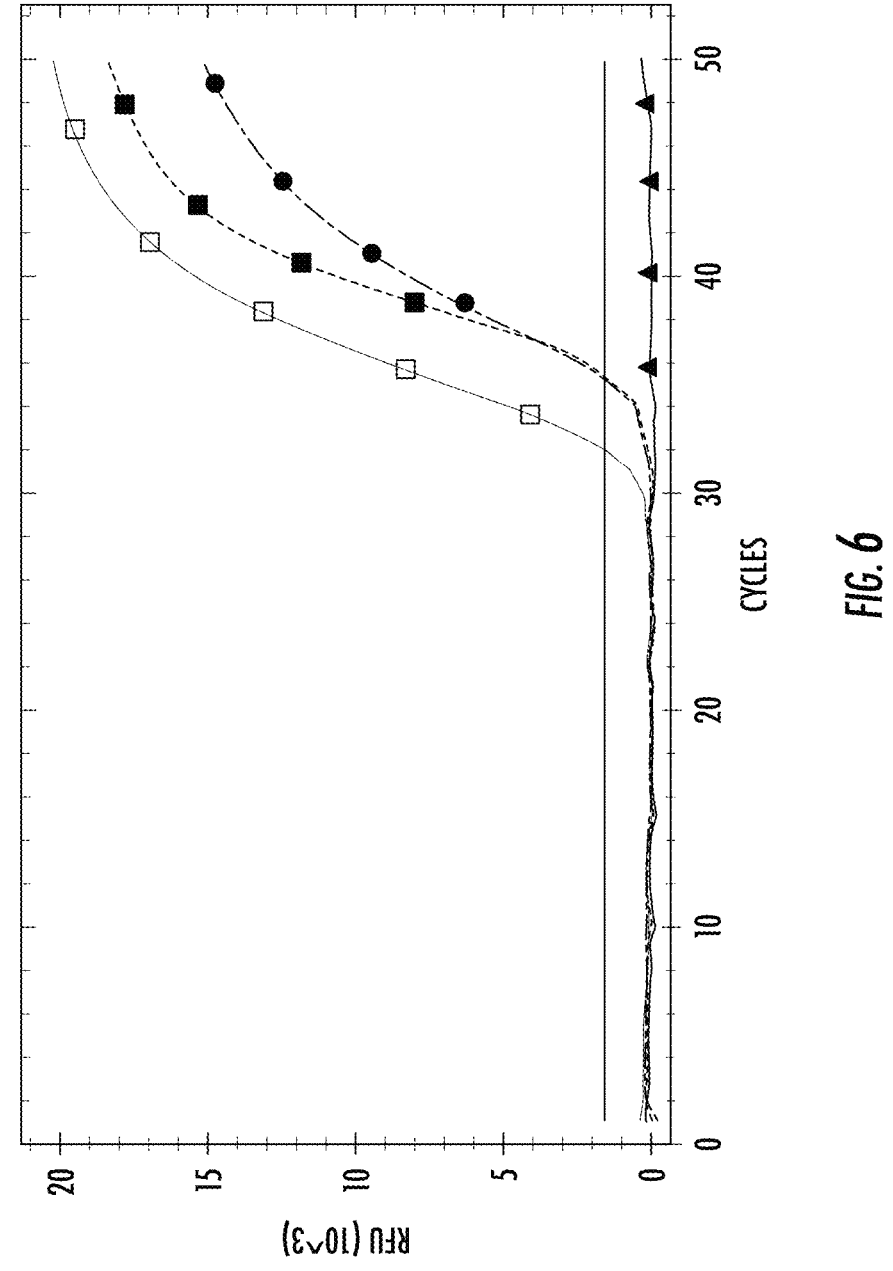
FIG. 6 substantially shows real-time PCR amplification curves for an environmental water sample analyzed with PVT-VIABLE.

FIG. 6 shows an example of the real-time PCR amplification curves for one PVT-VIABLE positive sample (filled squares—$T_0$, open squares $T_2$, filled circles-positive control, filled triangles-negative control). This sample had a $\Delta$Ct of 3.45 and the sample was also culture positive.

Figure 7:
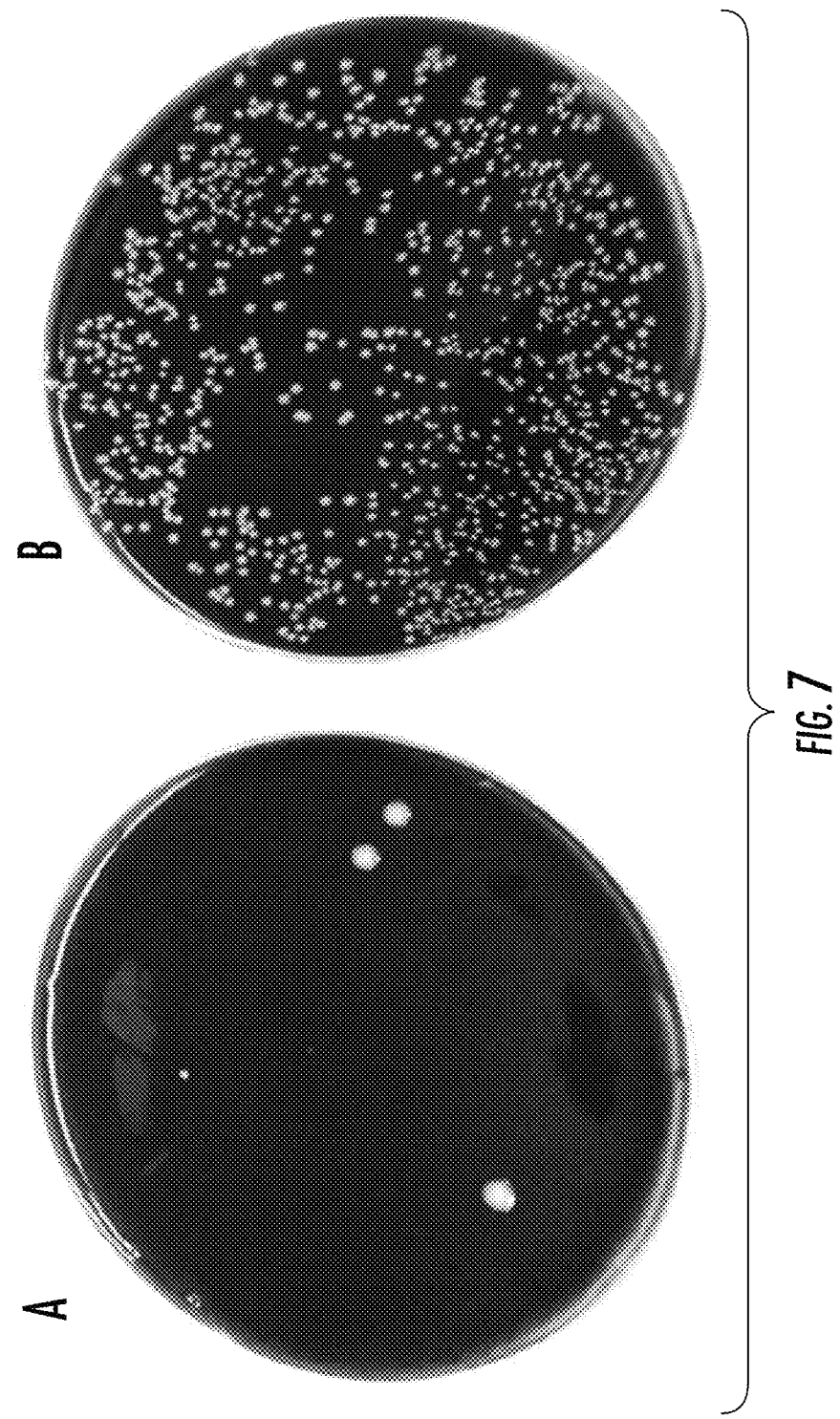
FIG. 7 substantially shows spread plate counts for an environmental sample analyzed with PVT-VIABLE.

FIG. 7 shows the spread plate counts corresponding to the real-time PCR data shown in FIG. 6 plated at $T_0$ (A. in FIG. 7) and $T_2$ (B. in FIG. 7). FIG. 7 shows the culture results for this sample increased in CFU/ml from 4 to >300.

TABLE 1

PVT-VIABLE beta testing results for
over 300 samples. 301 potable water

PVT-VIABLE Beta Test Statistics

| | |
|---|---|
| VIABLE+ and Culture+ | 30 |
| VIABLE+ and Culture– | 45 |
| VIABLE– and Culture+ | 2 |
| VIABLE– and Culture– | 194 |
| Culture+ | 32 |
| Culture– | 239 |
| VIABLE+ | 80 |
| VIABLE– | 220 |
| Total # of Samples | 301 |
| % culture+ | 10.63% |
| % VIABLE+ | 26.58% |
| Sensitivity | 97.56% |
| Positive Predictive Value | 40.00% |
| Negative Predictive Value | 98.98% | samples were analyzed by PVT-VIABLE and compared to the spread plating method on GVPC agar. VIABLE positive (VIABLE+) means the sample had a $\Delta$Ct$\geq$1.5 between the two real-time PCRs. That is, a $\Delta$Ct$\geq$approximately 1.5 between the $T_0$ and $T_2$ DNA extracts is considered to indicate the presence of the viable waterborne pathogen in the sample. Culture positive (culture+) means $\geq$1 colony was detected on the $T_0$ spread plate or the $T_2$ spread plate. For the PPV and NPV statistics, the culture result was set to true.

The results in table 1 show that PVT-VIABLE works well on real water samples and is surprisingly more sensitive than the traditional culture method. The sensitivity of the assay is very high at 97.56%; only 2 samples were false negative (VIABLE–/culture+) and these results were likely due to competing microbiota overgrowth. The NPV was 98.98% due to the 2 false negatives mentioned above. The PPV (set to culture=true) of the assay was strikingly low at 40% compared to ISO 11731 spread plates culture (40% of the samples that are VIABLE positive were also culture positive) and this is due to the 45 samples that were PVT-VIABLE positive and culture-negative (tentative culture method false negatives).

This statistic was calculated using "spread plate culture result=true". The ability of PVT-VIABLE to detect more viable *Legionella* samples than the traditional method, can be explained in two ways: 1.) PVT-VIABLE detected both viable and VBNC *Legionella*, therefore, many more positive results were obtained compared to spread plate cultures which detect only those bacteria that can form colonies on the plates, 2.) PVT-VIABLE detected viable *Legionella* at a lower limit of detection than the traditional spread plate methods. In reality then, the PVT-VIABLE method revealed that spread plate cultures returned many false-negative results because of the reasons discussed above. VIABLE positive, culture-negative samples are preliminary confirmation that VBNC cells can be resuscitated in the enrichment broth. An increase in DNA over the 40-48 h incubation time conclusively demonstrates cellular growth and is a more accurate and sensitive indication of the viability of an organism compared to the traditional definition of bacteria being able to form visible colonies on solid growth media.

Example 3—VBNC Resuscitation Experiment

Figure 8:
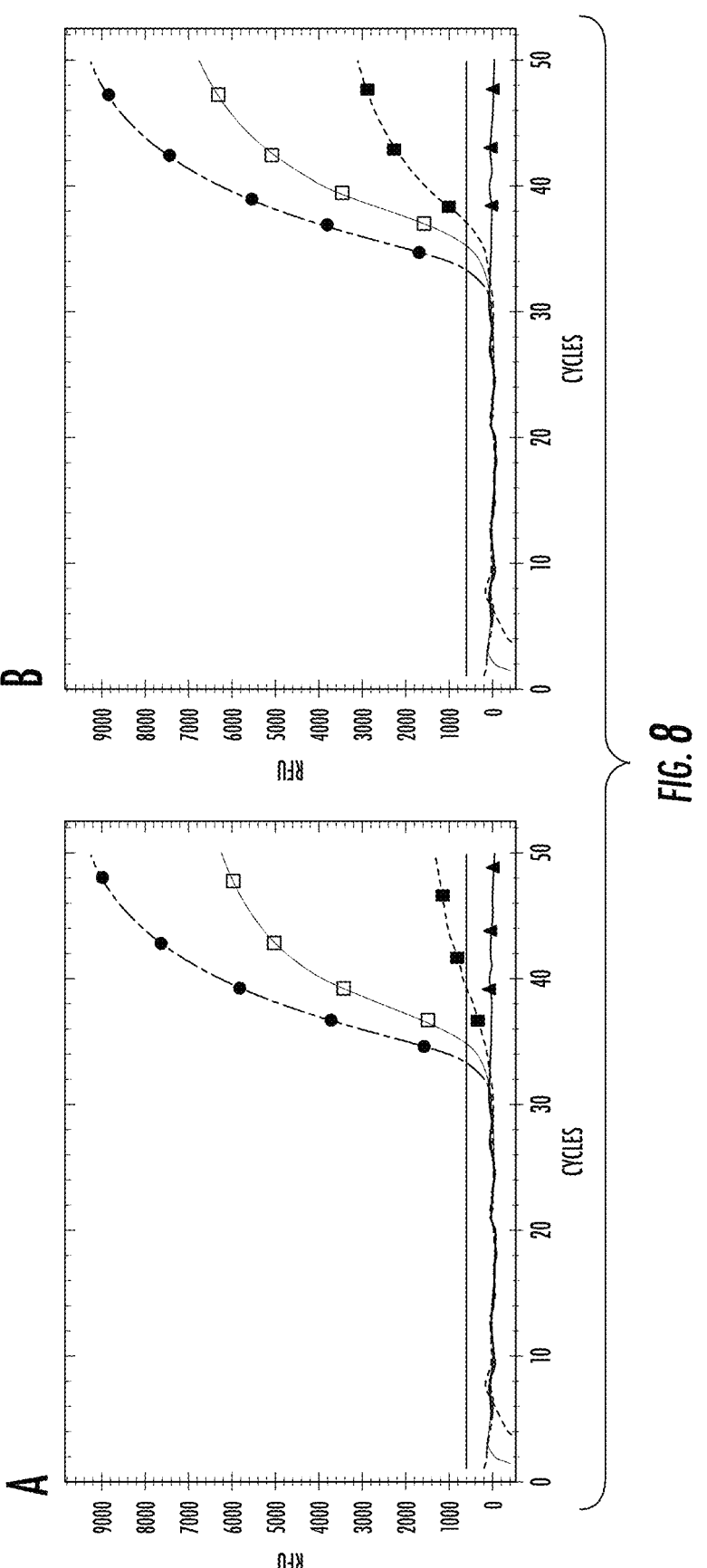
FIG. 8 substantially shows real-time PCR amplification curves for an environmental water sample analyzed with PVT-VIABLE and Amoeba co-culture.

A side-by-side experiment was designed to show the ability of PVT-VIABLE to resuscitate VBNC cells in comparison to resuscitation via co-culture with amoebae, the natural host for *Legionella*. Twenty-eight potable water samples from a chloraminated water system were analyzed by PVT-VIABLE and with amoeba co-culture in three separate experiments. In short, the same collection and preparation as PVT-VIABLE was done on the water sample, then the filter membrane was added to a flask containing 10 ml of PYG media and $10_3$ to $10_4$ cells/ml of *Acanthamoeba castellanii* (a natural host for *Legionella*) All samples were spread plated at $T_0$ and $T_2$. The same DNA extractions and real-time PCR were performed on the amoeba flasks and the PVT-VIABLE flasks. The $\Delta$Ct values for each method were compared. FIG. 8 shows the real-time PCR amplification curves for an environmental water sample analyzed with PVT-VIABLE (A. in FIG. 8) and Amoeba co-culture (B. in FIG. 8) (filled squares—$T_0$, open squares $T_2$, filled circles—positive control, filled triangles—negative control). A positive $\Delta$Ct for PVT-VIABLE and for amoeba co-culture with no CFUs on the spread plate at $T_0$ shows a resuscitation, growth, and infectivity of VBNC cells from an environmental water sample. According to the real-time PCR results there were seven VIABLE+/Amoeba+, two VIABLE–/Amoeba+, four VIABLE+/Amoeba–, and 15 VIABLE–/Amoeba– samples. The seven environmental samples that were VIABLE+/Amoeba+ and culture negative show VBNC resuscitation by PVT-VIABLE that was confirmed by amoeba co-culture.

The PVT-VIABLE approach described herein offers an innovative method for the determination of viable *Legionella* due to enrichment aspect and to the approach of measuring viability through the increase in nucleic acid concentration. This tandem approach has not been applied to *Legionella* and this approach differs from currently available technologies. This invention also improves upon existing technology by significantly decreasing the time it takes for a viable *Legionella* diagnostic. The current timeline is 10 days-14 days using prior art techniques. With the method as described herein, results will be available approximately 96 hours (4 days) after samples are taken from a facility. This method also improves on the prior art by resuscitating and detecting injured VBNC cells that would have otherwise gone undetected using traditional prior art techniques.

In one embodiment, results may be given as positive or negative for viable *Legionella* samples at a limit of detection (LOD) of 1 viable cell/100 ml (10 viable cells/L). Note that the volume of sample filtered determines the LOD. For example, if 1 L of sample is filtered, then the LOD is 1 viable cell/L of sample.

It can be seen from the foregoing examples that the $\Delta$Ct value between the $T_0$ and $T_2$ extracts determined by the described PVT-VIABLE method can be indicative of the presence of pathogens within a water sample, including viable but non-culturable cells. In the present examples, a $\Delta$Ct greater than approximately 1.5 provides a threshold requirement for indicating the presence of waterborne pathogens in the sample, specifically viable *Legionella*. The present inventors have conducted experiments to determine an appropriate value for ΔCt.

Out of 49 samples, 14 were positive for *Legionella*. There were 11 *Legionella* species and three *L. pneumophila* serogroup 2-14. Samples were taken from the following; 40 samples from bathroom sinks, 1 sample from a kitchen sink, five samples taken from showers and three samples taken from drinking fountains, which were all tested for the presence of *Legionella*. All 14 positives were detected as viable on the PCR with a ΔCt greater than 1.5. All but one of the 14 positive samples were detected as viable with the PCR with a ΔCt of 1.

TABLE 2

Samples analyzed using the ΔCt ≥ 1 cutoff value.

| SAMPLE STATISTICS ≥ 1 | # |
|---|---|
| True Positive (≥1 ΔCt) | 14 |
| False positive (N ISO, ≥1 ΔCt) | 1 |
| False negative (P ISO, but ≤1 ΔCt) | 0 |
| True Negative (N ISO and ≤1 ΔCt) | 34 |
| Total # of +ISO plate | 14 |
| Total # of –ISO plate | 35 |
| Total # of Samples | 49 |
| ISO+ AND VIABLE– | 4 |
| ISO– AND VIABLE– | 28 |
| Total # Shower | 5 |
| Total # Bathroom Sink | 40 |
| Total # Kitchen Sink | 1 |
| Total # Drinking Fountain | 3 |
| PREVALENCE OF *Legionella* positives | 28.57% |
| SENSITIVITY | 100.00% |
| POSITIVE PREDICTIVE VALUE (≥1 ΔCt correlates to P ISO) | 93.33% |
| Negative Predictive Value (N PCR correlates to N ISO) | 87.50% |

TABLE 3

Samples analyzed using the ΔCt ≥ 1.5 cutoff value. Increasing the cut off to ≥1.5 ΔCt the PPV was 100% and it retained 100% sensitivity

| SAMPLE STATISTICS ≥1.5 | # |
|---|---|
| True positive (≥1.5 ΔCt) | 14 |
| False positive (N ISO, ≥1.5 ΔCt) | 0 |
| False negative (P ISO, but ≤1.5 ΔCt) | 0 |
| True Negative (N ISO and ≤1.5 ΔCt) | 35 |
| Total # of +ISO plate | 14 |
| Total # of –ISO plate | 35 |
| Total # of Samples | 49 |
| ISO+ AND VIABLE– | 4 |
| ISO– AND VIABLE– | 28 |
| Total # Shower | 5 |
| Total # Bathroom Sink | 40 |
| Total # Kitchen Sink | 1 |
| Total # Drinking Fountain | 3 |
| PREVALENCE OF *Legionella* positives | 28.57% |
| SENSITIVITY | 100.00% |
| POSITIVE PREDICTIVE VALUE (≥1.5 ΔCt correlates to P ISO) | 100.00% |
| Negative Predictive Value (N PCR correlates to N ISO) | 87.50% |

TABLE 4

Samples analyzed using the ΔCt ≥ 2 cutoff value. Increasing the cut off to ≥2 ΔCt, one PVT-VIABLE positive was missed, lowering the sensitivity to 92.86%.

| SAMPLE STATISTICS ≥ 2 | # |
|---|---|
| True Positive (≥2 ΔCt) | 13 |
| False positive (N ISO, ≥2 ΔCt) | 0 |
| False negative (P ISO, but ≤2 ΔCt) | 1 |
| True Negative (N ISO and ≤2 ΔCt) | 35 |
| Total # of +ISO plate | 14 |
| Total # of –ISO plate | 35 |
| Total # of Samples | 49 |
| Biplate positive | 4 |
| *Legionella* species | 28 |
| Total # Shower | 5 |
| Total # Bathroom Sink | 40 |
| Total # Kitchen Sink | 1 |
| Total # Drinking Fountain | 3 |
| PREVALENCE OF *Legionella* positives | 28.57% |
| SENSITIVITY | 92.86% |
| POSITIVE PREDICTIVE VALUE (≥2 ΔCt correlates to P ISO) | 100.00% |
| Negative Predictive Value (N PCR correlates to N ISO) | 87.50% |

It can be seen from Tables 2-4 that setting the cut off value of ΔCt can have an impact on the usefulness of the results. If the value of ΔCt is set too low, then the sensitivity is high, but false positives may be recorded. Increasing the cut-off value of ΔCt above 1 reduces the false positives but increasing the cut-off value of ΔCt excessively leads to reduced sensitivity and the introduction of false negatives. Through experiment, the present inventors have found that a cut-off value for ΔCt should be in the range 1<=ΔCt>=2. Preferably, the cut-off value should be approximately ΔCt=1.5.

While the specification makes specific reference to detecting *Legionella* bacteria, the PVT-VIABLE technique, based on enrichment of targeted pathogens, may be used to determine the presence of other types of waterborne pathogens. Targeting of alternative pathogens may be achieved through selection of different filtering membranes, different enrichment cultures and experimental determination of appropriate incubation parameters, ΔCt cut-off values, etc. Other pathogens of note would be non-tuberculosis *Mycobacteria, Pseudomonas aeruginosa, Salmonella, E. coli*, among others. The ΔCt cutoff value of 1.5 is appropriate for *Legionella* and for an incubation period of 40-48 hours. Other waterborne pathogens may have a different derived ΔCt than *Legionella* but the principle of the matter (the change in DNA concentration) remains the same. That is, the ΔCt cutoff may be different for different organisms. For example, the ΔCt cut-off value may be larger in some samples that grow very well in the media. Alternatively, or in addition, incubation periods may be altered to account for the different growth rate of the target organism in the medium. For example, the target organism is *Pseudomonas* (another waterborne pathogen) then the incubation could be shorter because the doubling time for *Pseudomonas* is shorter.

The membrane filter should be 0.2 μm in order to capture the bacteria. 0.45 μm can also be used, but some bacteria may be missed. The sample size shouldn't be less than 100 ml but can be higher than that if it is determined that it is necessary.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A process for detecting presence of viable non-culturable targeted waterborne pathogens comprising:

(A) obtaining a liquid sample;

(B) collecting a concentrate of bacterial cells from the liquid sample;

(C) enriching the concentrate of bacterial cells to produce an enriched concentrate of bacterial cells;

(D) extracting a $T_0$ DNA extract from the enriched concentrate of bacterial cells at time $T_0$;

(E) storing the $T_0$ DNA extract;

(F) incubating the enriched concentrate of bacterial cells;

(G) extracting a $T_2$ DNA extract from the incubated enriched concentrate of bacterial cells at time $T_2$;

(H) analyzing the $T_0$ DNA extract with real-time Polymerase Chain Reaction (PCR) to determine a cycle threshold Ct value for the $T_0$ DNA extract;

(I) analyzing the $T_2$ DNA extract with real-time Polymerase Chain Reaction (PCR) to determine a cycle threshold Ct value for the $T_2$ DNA extract; and (J) analyzing a difference in Ct value ($\Delta$Ct) between the $T_0$ DNA extract and the $T_2$ DNA extract to determine a qualitative assessment of the presence of viable but not culturable cells of the targeted waterborne pathogens in the liquid sample.

2. The process of claim 1 wherein the qualitative assessment comprises determining if the $\Delta$Ct is greater than a cut-off value.

3. The process of claim 2 wherein the cut-off value is $\Delta$Ct is greater than approximately 1.5.

4. The process according to claim 1 comprising:

(A) obtaining the liquid sample from a water source; and (B) neutralizing residual oxidants and antimicrobials within the liquid sample to obtain a substantially oxidant-free antimicrobial sample.

5. The process according to claim 4, wherein the sample is neutralized using a reducing agent.

6. The process according to claim 5 wherein the reducing agent comprises at least one of sodium thiosulfate ($Na_2S_2O_3$) or sodium bisulfite.

7. The process of claim 1 wherein collecting the concentrate of bacterial cells comprises performing a filter concentration on the liquid sample.

8. The process of claim 7 wherein the filter concentration comprises using a membrane in a filtration unit, aseptically removing the membrane from the filtration unit and providing the membrane into an enrichment broth.

9. The process according to claim 8, wherein the membrane is a polycarbonate membrane.

10. The process according to claim 9, wherein the polycarbonate membrane is a track-etched membrane.

11. The process according to claim 10, wherein the polycarbonate membrane has a pore size of less than 0.25 µm.

12. The process according to claim 4, wherein the polycarbonate membrane has a diameter of about 47 mm or larger.

13. The process according to claim 1, wherein the concentrate of bacterial cells is enriched in a solution of growth medium.

14. The process according to claim 13, wherein the growth medium is a Buffered Yeast Extract media comprising Vancomycin, Polymyxin, Cycloheximide, Glycine, Iron pyrophosphate, L-cysteine, and Bovine serum albumin.

15. The process according to claim 1, wherein the $T_0$ DNA extract is stored at about $-20°$ C.

16. The process according to claim 1, wherein the concentrate of bacterial cells is incubated at a temperature from $30°$ C. to $37°$ C.

17. The process according to claim 1, wherein the concentrate of bacterial cells is shaken at 50 rpm during the incubation period.

18. The process according to claim 1, when the Ct value of $T_2$ DNA extract is equal to or greater than the Ct value of $T_0$ DNA extract, the sample is assessed to not contain viable but not culturable cells of the targeted waterborne pathogens.

19. The process according to claim 1, when the Ct value of $T_2$ DNA extract is less than the Ct value of $T_0$ DNA extract, the sample is assessed to contain viable but not culturable cells of the targeted waterborne pathogens.

20. The process according to claim 1 comprising:

(A) diluting the $T_0$ DNA extract;

(B) detecting PCR amplification by performing real-time PCR on the $T_0$ DNA extract dilution;

(C) repeating the diluting and detecting until no PCR amplification is detected;

(D) wherein the highest dilution of the $T_0$ DNA extract at which PCR amplification is detected provides an order of magnitude quantification of the viable but not culturable cells of the targeted waterborne pathogen in the liquid sample.

21. The process according to claim 20, when only the $T_0$ DNA extract shows PCR amplification, the quantification of the liquid sample is ≤1 Colony Forming Units (CFU)/ml.

22. The process according to claim 20, wherein the dilution is a serial dilution of 10-fold to 100-fold.

23. The process according to claim 22, wherein when only both the $T_0$ DNA extract and a 1:10 dilution of the $T_0$ DNA extract show PCR amplification, the quantification X of the liquid sample is 1<X≤10 CFU/ml.

24. The process according to claim 22, wherein when each of the $T_0$ DNA extract, the 1:10 dilution of the $T_0$ DNA, and a 1:100 dilution of the $T_0$ DNA show PCR amplification, the quantification X of the liquid sample is 10<X≤100 CFU/ml.

25. The process according to claim 1, wherein the targeted pathogen is *Legionella*.

* * * * *